United States Patent [19]
Lewis

[11] Patent Number: 4,823,591
[45] Date of Patent: Apr. 25, 1989

[54] CALIBRATION METHOD FOR EXHAUST MASS FLOW MEASURING SYSTEM

[75] Inventor: Gary W. Lewis, Fountain Valley, Calif.

[73] Assignee: Horiba Instruments Incorporated, Irvine, Calif.

[21] Appl. No.: 118,195

[22] Filed: Nov. 5, 1987

[51] Int. Cl.[4] .............................................. G01F 25/00
[52] U.S. Cl. ......................................................... 73/3
[58] Field of Search ............................................... 73/3

[56] References Cited

U.S. PATENT DOCUMENTS

| | | | |
|---|---|---|---|
| 2,755,663 | 7/1956 | Smith et al. | 73/3 X |
| 3,144,769 | 8/1964 | Francisco, Jr. | |
| 3,407,646 | 10/1968 | Traver | 73/23 |
| 3,469,442 | 9/1969 | Brueckner | 73/3 X |
| 3,603,155 | 9/1971 | Morris et al. | 73/23 X |
| 3,699,814 | 10/1972 | Kaufman. | |
| 3,741,009 | 6/1973 | Burdeaux | 73/3 X |
| 3,750,472 | 8/1973 | Ducousset | 73/3 X |
| 3,817,100 | 6/1974 | Anderson et al. | |
| 3,924,445 | 12/1975 | Konomi et al. | 73/3 |
| 3,965,749 | 6/1976 | Hadden et al. | |
| 3,975,953 | 8/1976 | Smith et al. | 73/118.1 |
| 3,986,386 | 10/1976 | Beltzer et al. | 73/28 |
| 4,226,675 | 10/1980 | Lewis et al. | |
| 4,341,107 | 7/1982 | Blair et al. | 73/3 |
| 4,351,181 | 9/1982 | Currans | 73/23 |
| 4,379,402 | 4/1983 | Harman, III | 73/23 |
| 4,586,367 | 5/1986 | Lewis | 73/28 X |
| 4,637,366 | 1/1987 | Cowles | 123/440 X |
| 4,706,492 | 11/1987 | Jones, Jr. et al. | 73/3 |

FOREIGN PATENT DOCUMENTS 0208045 1/1987 European Pat. Off.

Primary Examiner—Tom Noland
Attorney, Agent, or Firm—Harness, Dickey & Pierce

[57] ABSTRACT

A testing apparatus for sampling the emission content of the source when a portion of the exhaust gas is optionally diluted using clean dry air added near the sample extraction point. A sonic venturi is used to establish a constant mass flow rate from the exhaust system of the engine under test and a subsonic venturi monitors the flow rate of dilution air. Both venturis provide flow rate signals which are substracted to determine the flow rate of the exhaust.

4 Claims, 4 Drawing Sheets

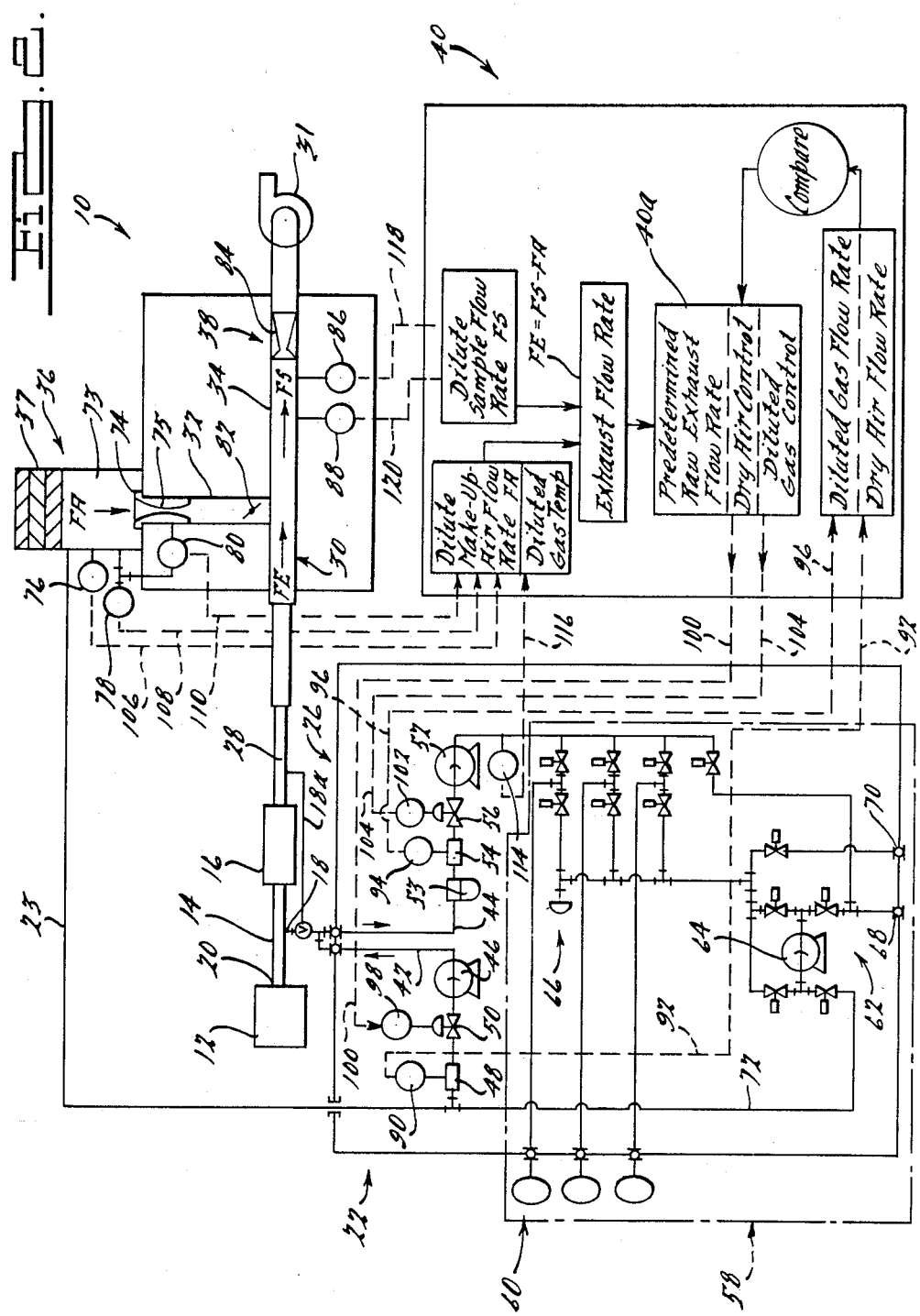

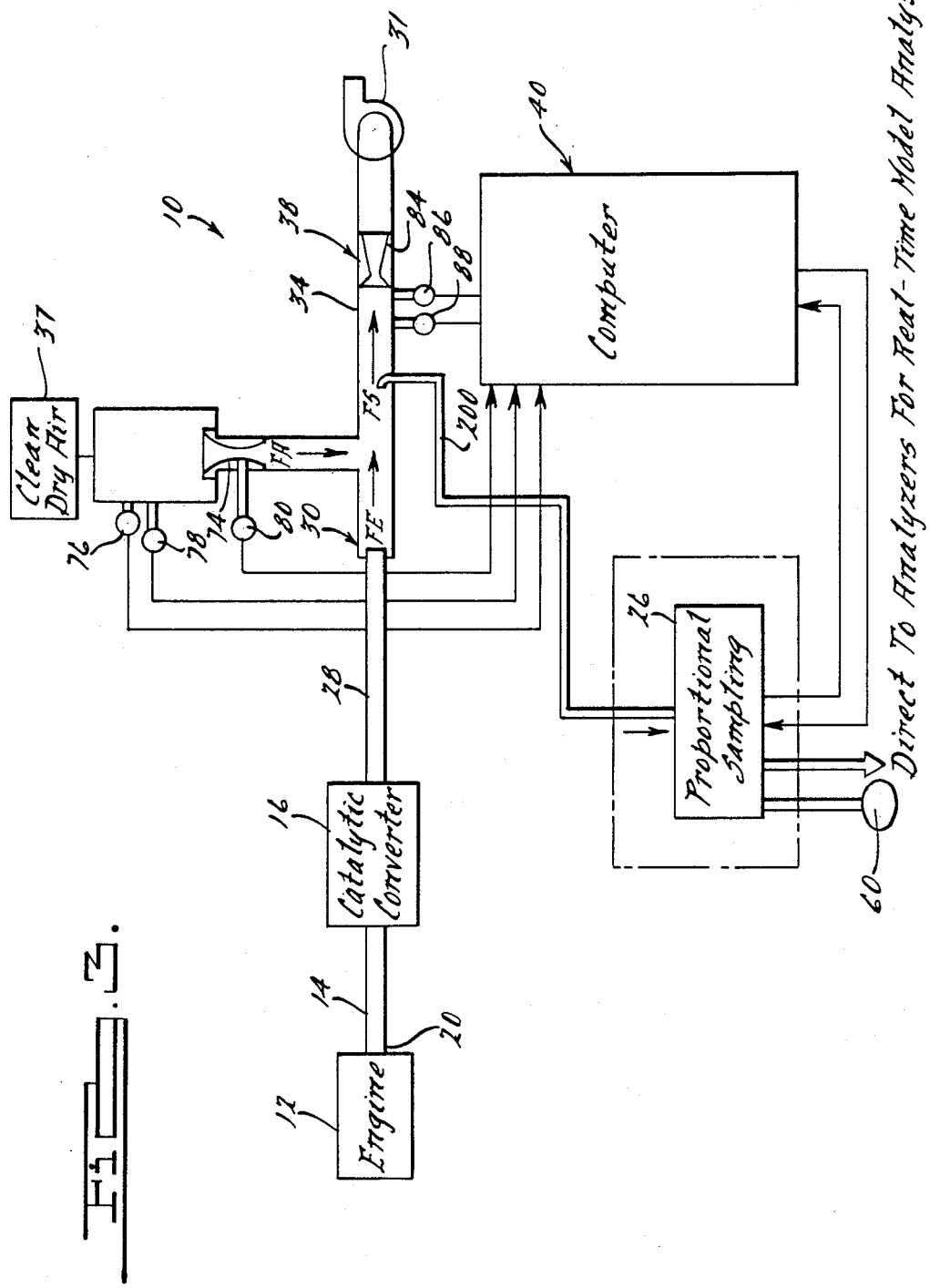

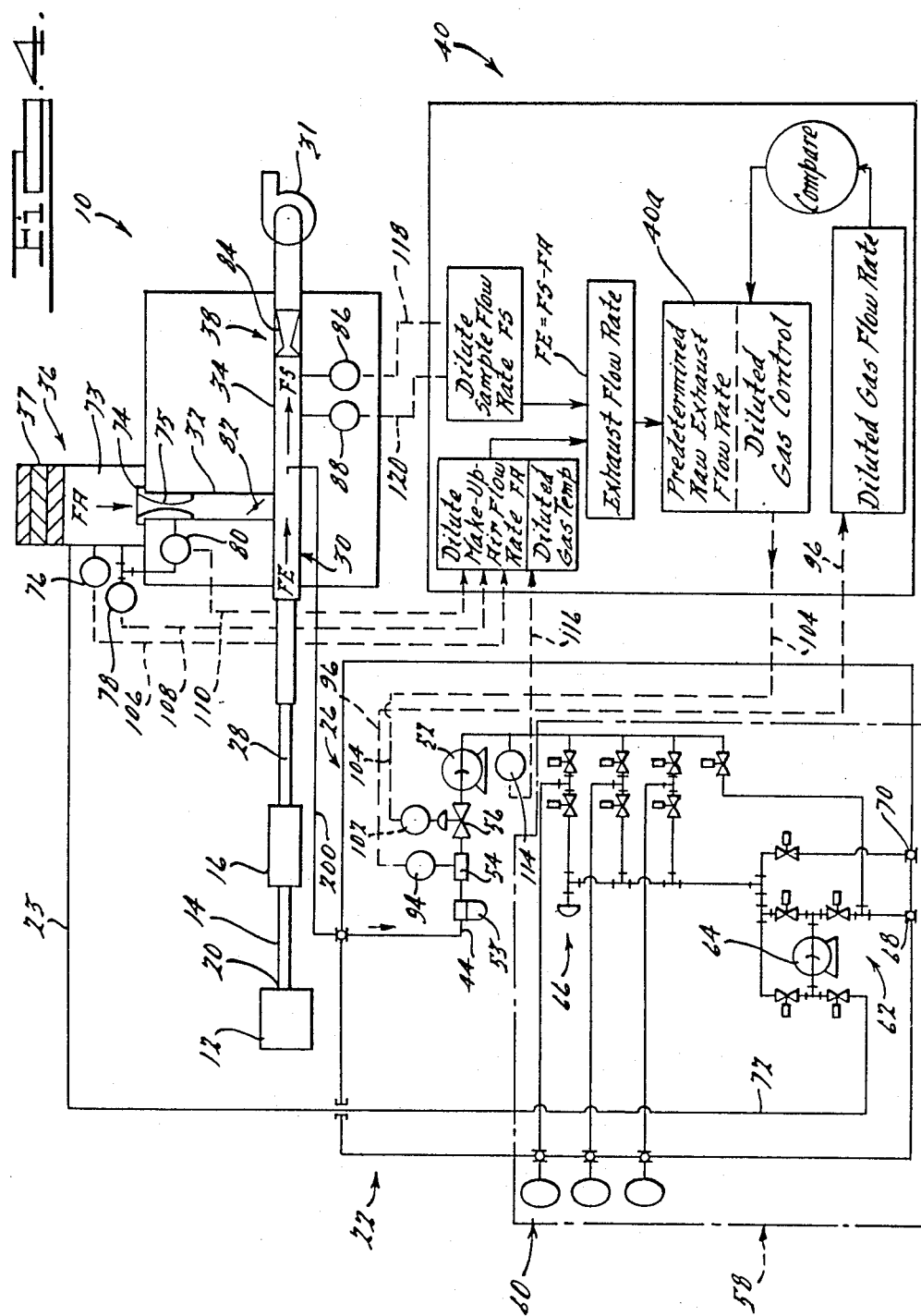

CALIBRATION METHOD FOR EXHAUST MASS FLOW MEASURING SYSTEM

BACKGROUND AND SUMMARY OF THE INVENTION

The present invention relates to equipment for measuring the exhaust emissions of internal combustion engines, and more particularly to an apparatus for measuring the contaminate contents of exhaust emissions utilizing a subsonic and sonic flow venturi metering system and means for introducing clean dry air to minimize error due to condensation.

Under present day federal regulations the exhaust emissions from motor vehicles must not exceed specified values of certain contaminates. See Section 1201, Chapter XII, Title 45 of the Code of Federal Regulations, as published in the Federal Register, Vol. 36, No. 128, Friday, July 2, 1971, at pages 12652 et seq. See also Kaufman, U.S. Pat. No. 3,699,814.

The presence of such standards had made it imperative that the exhaust emissions from vehicle engines be tested and analyzed to determine the relative amount of impurities therein. Much effort has gone into the development of equipment for use in this field of exhaust sampling, and it is now known to deliver exhaust gases from an internal combustion engine at an accurately measured flow rate through a test apparatus for purposes of determining and analyzing the relative amounts of impurities. The general scheme of such testing is to utilize a device such as a critical flow venturi to maintain a constant mass flow of diluted sample gas through the apparatus; the diluted sample gas is comprised of the vehicle exhaust gas and dilution air. The admission of dilution air cools the sample, reduces the relative moisture content to eliminate condensation in the sample storage units, and thereby makes the sample easier to work with. The diluted sample is then distributed to various sample storage units for subsequent chemical analysis. Because of the varying amount of vehicle exhaust flow rate during the prescribed driving cycles, the amount of dilution air will also change (higher exhaust flow rate requires lower dilution air, and vice versa) due to the constant mass flow device in the apparatus; to make the tests meaningful, the driving cycles are precisely defined.

A system which satisfies these general requirements is described in the above identified portion of the Federal Register. However, the system described in the Federal Register suffers a number of difficulties and disadvantages, which are discussed in U.S. Pat. No. 3,699,814, to Kaufman, entitled "Gas Sampler," issued Oct. 24, 1972, and now assigned to the assignee of the present invention. The Kaufman patent, the disclosure of which is incorporated herein by reference, taught a much improved gaseous exhaust emissions sampler which replaced the troublesome constant displacement pump of prior systems with a critical flow venturi for metering the diluted exhaust emissions at a constant volume flow.

One problem with lowering the sample temperature is that the cooler sample cannot carry as much water vapor as the heated sample did, with the result that some of the water vapor condenses in the sampling apparatus. This condensation directly affects the volumetric flow through the sampling apparatus with a corresponding loss of accuracy. The conventional technique for addressing this problem is to use heated sample lines to prevent condensation. Heated sample lines are difficult to maintain and add greatly to the complexity of the sampling system.

In addition to the moisture problem and for real-time (modal) testing, there has been a problem with maintaining system precision and accuracy in the dilution air admission system. As stated above, the admission of dilution air must be done with accuracy; and the act of performing the exhaust emission test on the engine must not appreciably alter the engine's operation, otherwise the test results would not be accurate. For example, the exhaust testing apparatus should not place undue back pressure or suction on the engine exhaust system, otherwise the engine would not be operating as it would under normal operating conditions. Conventional exhaust analyzers have had problems in this regard, since conventional flow meters used in such analyzers require high pressures in order to operate in the most accurate range. The need to use conventional flow meters in a comparatively high pressure environment has presented problems in interfacing the high pressure environment of the meter with the engine exhaust system.

Some prior art techniques also utilize tracer methods (carbon dioxide or other nonreactive gases) in which two independent analyzers are used. Such techniques are not considered to be generally satisfactory. In addition, prior art techniques are based on certain assumptions which may not be true in practice, namely that the analyzers introduce no calibration errors and that there are no leaks in the system. There has heretofore been no effective way of calibrating to ensure that these errors and leaks are not inherent in the test system.

Accordingly, the present invention provides an apparatus and method for calibrating an apparatus for measuring the exhaust mass flow of an internal combustion engine having an exhaust conduit. The apparatus includes a test conduit having an exhaust inlet coupled with the exhaust conduit. A subsonic venturi is coupled to the test conduit for enabling passage of fluid. Transducers are coupled with the subsonic venturi for providing signals. A sonic venturi is coupled to the test conduit for enabling passage of fluid. Transducers are coupled with the sonic venturi for producing signals. A computer is coupled with the transducers for interpreting the signals.

The method comprises capping the exhaust inlet of the test conduit; causing a quantity of fluid to flow through the subsonic venturi, through the test conduit, and through the sonic venturi; measuring the flow through the sonic venturi to produce a first signal; measuring the flow through the subsonic venturi to produce a second signal; comparing the first signal and second signal to determine an error; adjusting either of the first or second signals to null the error and to thereby calibrate the apparatus.

Further, the present invention provides an apparatus and method for extracting a proportional sample of exhaust gas from an internal combustion engine. An extraction member is coupled with the engine for providing a confinement path for the sample. A mechanism is coupled with the extraction member for providing clean dry air into the extraction member. A measuring mechanism is coupled with the first mechanism for providing clean dry air into the extraction member. The measuring mechanism produces a first signal. A second measuring mechanism produces a second signal. A computer is coupled with both the measuring mechanisms for interpreting the signals produced. The method comprises extracting a sample of exhaust gas from the internal combustion engine; passing the sample into the extraction member; mixing the sample with a quantity of clean dry air; measuring the quantity of clean dry air with the exhaust sample to produce a first signal; measuring the quantity of the mixed clean dry air and exhaust sample to produce a second signal; determining a ratio of the clean dry air to the exhaust sample; comparing the ratio of the first and second signals with a predetermined ratio to determine an error; and adjusting either the first or second signals to null the error and to thereby produce a proportional sample of exhaust gas.

An advantage of this system is that it provides a means of measuring diluted raw samples on a real time basis using analyzers on same ranges as used for bag analysis. The advantage is a cost savings of several analyzers (or possibly a complete/separate system) for raw only samples.

It is possible to eliminate the need for bag sampling (sample storage units) entirely by integrating the real time gas analyzer readings over the EPA required driving cycles, again resulting in cost savings of the required bag sampling system to the customer. Correlation to the conventional bag sampling system is required, however, if test results are to be used for testing to present EPA requirements.

For a more detailed understanding of the invention, its objects and advantages, references, may be had to the following description and to the accompanying drawings.

BRIEF DESCRIPTION OF THE DRAWINGS

FIG. 2 is a more detailed schematic flow diagram illustrating the invention in a raw exhaust sampling system.

FIG. 3 is a diagrammatic illustration of a dilute exhaust sampling system in accordance with the invention.

FIG. 4 is a more detailed schematic flow diagram illustrating the invention in a dilute exhaust sampling system.

DESCRIPTION OF THE PREFERRED EMBODIMENT

Figure 1:
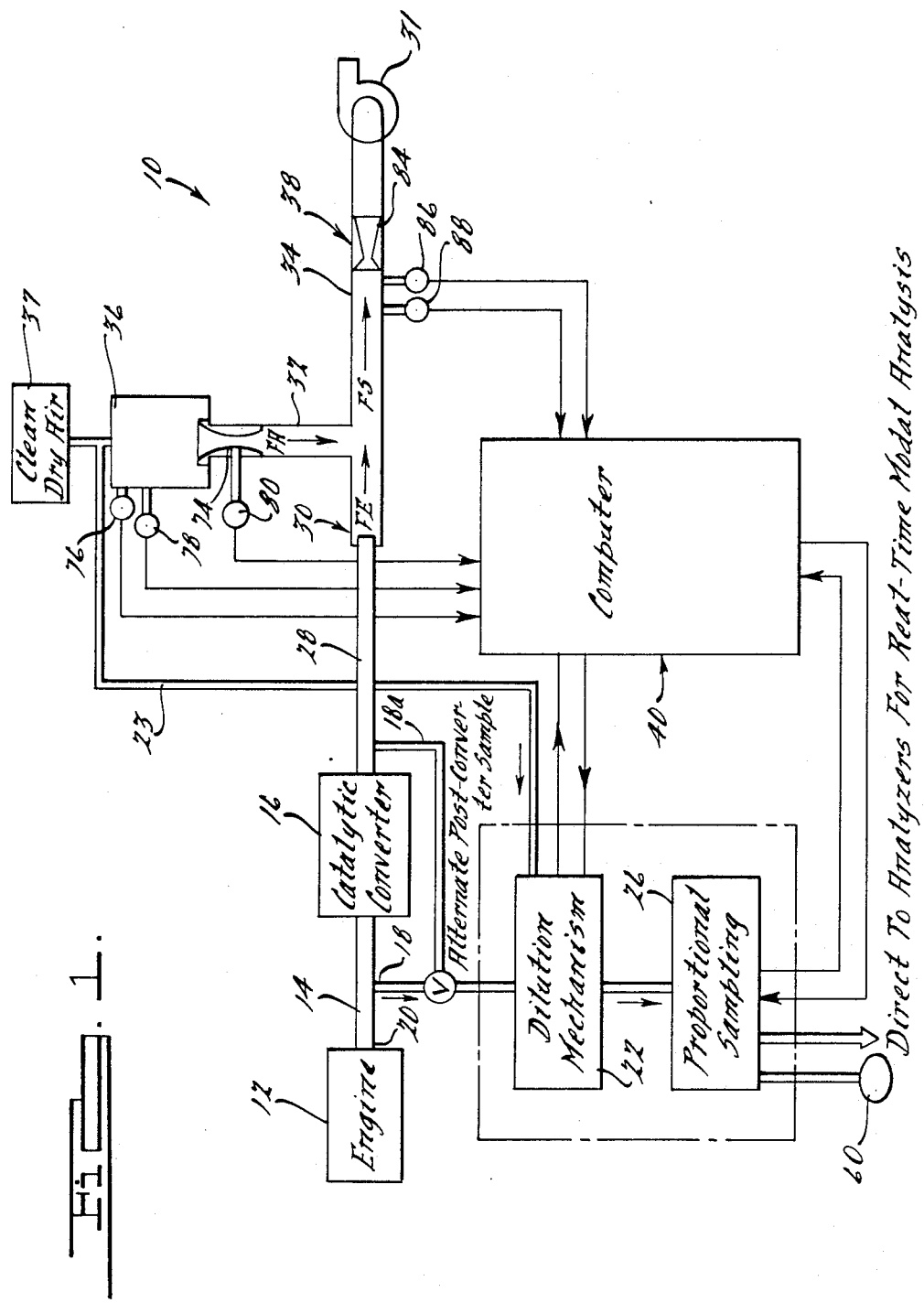
FIG. 1 is a diagrammatic illustration of a raw exhaust sampling system utilizing the present invention.

Referring to FIG. 1, a system for measuring the proportional content of a source is illustrated and designated by reference numeral 10. Connected to the system is an internal combustion engine source 12 which exits its raw exhaust into an exhaust conduit 14. In the case of a gasoline engine, the exhaust conduit 14 may also include a catalytic converter 16 and further exhaust pipe or tail pipe 28. A sample extraction member 18 is coupled for sampling near the outlet point 20 of the engine source 12 either upstream (18) or downstream (18a) of the catalytic converter 16. A dilution mechanism 22 for adding clean dry air to the sample is coupled to the extraction member 18. Dilution mechanism 22 adds clean dry dilution air at a point very near the point at which extraction mechanism 18 takes the sample. The early admission of dry dilution air minimizes condensation and eliminates the need for heated sample lines. A proportional sampling mechanism 26 having an optional sample test bag 60 is coupled with the dilution mechanism 22 for collecting the sample, or directly to analyzers for real-time modal analysis.

System 10 further includes a test conduit 30 which is secured to the end of the tailpipe 28. The test conduit 30 tees, forming two legs 32 and 34. Dilution air is injected via a filtration system 37 into leg 32. A mechanism 36 for measuring the flow rate of the injected dilution air is coupled with leg 32 of the test conduit 30. Mechanism 36 includes a subsonic venturi 74. The measuring mechanism 36 is also coupled via conduit 23 with the dilution mechanism 22, which will be explained herein.

A mechanism 38, for measuring the flow rate of the entire bulkstream exhaust gas plus injected dilution air, is coupled with leg 34 of the test conduit 30. Mechanism 38 includes a sonic venturi 84. A blower 31 is coupled with the test conduit 30 for pulling a vacuum on the system, urging flow through the test conduit 30 and establishing a constant mass flow rate by virtue of sonic venturi 84. Because the subsonic venturi 74 is accurate without requiring a large pressure drop across it, the vacuum established by blower 31 at the system inlet 30 or end of tail pipe 28 can be quite low. Thus the engine under test is affected very little by the inclusion of this test system. The dilution mechanism 22, proportional sampling mechanism 26, measuring mechanism 36, and bulkstream flow measuring mechanism 38 are coupled with a computer 40 by means of pressure and temperature transducers 76, 78, 80, 86 and 88, and electrically operated solenoid valves and flow meters (shown only in FIG. 2).

Turning to FIG. 2, a detailed schematic in accordance with the present invention is shown. The extraction member 18 (18a) is positioned near the engine outlet port 20. The portion of exhaust gas, extracted at this point, generally has a temperature ranging from 500°–700° F. and a moisture content of approximately 20 percent.

The dilution mechanism shown generally at 22 has elements coupled with a conduit 42, upstream from the connection with the extraction member 18, and has elements coupled with a conduit 44 downstream from the connection with the extraction member 18.

Mechanism 22 includes a pump 46 for drawing clean dry air into the system through filtration system 37 via conduit 23. Also, mechanism 22 includes a flow meter 48 for metering the amount of dry air brought into the system. The flow meter 48 is associated with and transmits signals to the computer 40. Further, mechanism 22 includes a flow control valve 50 for controlling the flow in the conduit 42. The flow control valve 50 is associated with and controlled by the computer 40.

Dry air is drawn into the conduit 42 by the pump 46. The dry air travels along the conduit 42 until it joins member 18 and mixes with a portion of exhaust combustion gas extracted by member 18. The portion of the exhaust gas ranges in temperature from 500°–700° F. and has a moisture content of approximately 20 percent. Once the dry air mixes with the portion of exhaust gas the temperature is substantially lowered, eliminating the need for a heat exchanger or a cooling apparatus, and the moisture content is reduced to approximately 5 percent. With the moisture content thus substantially lowered, condensation problems are virtually eliminated.

The proportional sampling mechanism 26 draws a preselected ratio of dry air and exhaust gas for analysis and includes a pump 52 for drawing the diluted gas through conduit 44. The term diluted gas means the combination of dry air and the extracted portion of the exhaust gas. Also, proportional sampling mechanism 26 includes a flow meter 54 and control valve 56 both of which are positioned along conduit 44 for metering and controlling, respectively, the diluted gas and a particulate filter 53. Both the flow meter 54 and control valve 56 are coupled with the computer 40.

The diluted gas continues through conduit 44 into a flow directing circuit 58 shown generally within dashed lines. The flow directing circuit 58 includes several conduits and valves for enabling a portion of the diluted gas or all of the diluted gas to be either sampled or to be stored in storage bags 60 for further analysis. Also included in the flow directing circuit 58 is a purge device 62. This device 62 evacuates and flushes the sample bags 60 so that a new sample can enter into the bags 60 without being contaminated by prior samples. The purge device 62 includes a pump 64, and several solenoid valves, as shown in FIG. 2, for opening and closing the particular conduits leading to the sample bag 60 which are to be flushed or evacuated. Flow directing circuit 58 also includes a vacuum switch 66 for performing system leak checks, and conduits 68 and 70 which provide access to the diluted gas for venting the diluted gas to the atmosphere, or for transferring the diluted gas to transient analyzers for a real time analysis of the diluted gas, or for venting the diluted gas to the bench for any other desired tests. Flow directing circuit 58 receives clean dry air via conduit 72 for flushing the system.

The dilute flow measuring mechanism 36 includes a subsonic venturi 74, positioned in the first leg 32 of the test conduit 30. The subsonic venturi 74 is used for measuring the dilution "make-up" air flow rate FA. The subsonic venturi 74, with its inherent high accuracy and low pressure drop, enables the dilution air flow rate to be repeatedly determined. A temperature transducer 76 and a pressure transducer 78 are adjacently positioned on the air plenum 73 upstream from the subsonic venturi 74 and a second pressure transducer 80 is positioned at the throat 75 of the subsonic venturi 74. All three transducers are coupled with the computer 40 for determining the flow rate through venturi 74 by known computations.

The second leg 34 of the test conduit 30 includes the bulkstream flow measuring mechanism 38. The mechanism 38 includes a sonic venturi 84 and temperature and pressure transducers 86 and 88, respectively. The sonic venturi 84, as explained in the Kaufman patent referenced above, controls and stabilizes the bulkstream flow through the test conduit 30 and limits the flow in the test conduit 30, independent of the downstream vacuum, by virtue of a sonic flow at its throat. Sonic flow (i.e., critical flow) is maintained by producing a sufficient vacuum at the venturi exit by means of the centrifugal blower 31. The result is a constant mass flow device. Thus, by knowing the temperature and pressure upstream of the sonic venturi 84, the flow rate FS of the diluted sample can be calculated using known computations. Temperature and pressure transducers 86 and 88, positioned in the second leg of the test conduit 30, upstream from the sonic venturi 84, are coupled with the computer for performing the computations.

A calibration valve 82 is positioned in the first leg 32 of the test conduit 30. The calibration valve 82 enables the subsonic venturi 74 of the flow measuring mechanism 36 to zero calibrate the sonic venturi 84 of the bulkstream flow measuring mechanism 38. The zeroing process is accomplished by drawing dry air through the measuring mechanism 36 while the engine 12 is not running and with the tail pipe inlet side of conduit 30 plugged or capped. With the engine 12 turned off, and with no portion of exhaust gas entering into the dilution mechanism 22, the dry air is pumped through air plenum 73 and through subsonic venturi 74. The computer 40, through temperature and pressure transducers 76, 78 and 80, calculates the flow rate of the dry air through the subsonic venturi 74. The computer 40, through temperature and pressure transducers 86 and 88, calculates the flow rate of dry air through the sonic venturi 84 of the bulkstream flow measuring mechanism 38. The computer 40 determines and compares the two flow rates through the subsonic and sonic venturi 74 and 84. Theoretically, the amount of gas flow through the sonic venturi 84 should equal the amount of flow through the subsonic venturi 74. If the bulkstream flow through the sonic venturi 84 is other than equal to the flow through the subsonic venturi 74, the computer 40 can be adjusted so that the readings will be equal. By equalling the readings, through the subsonic and sonic venturis 74 and 84, a zero error will exist at the start up point of the system analysis. This provides the invention with very good calibration accuracy since the two venturis are calibrated to each other instead of to a third reference.

Generally, the computer 40 provides several functions as follows. The computer is used to determine the proportion of the air to sample ratio. A predetermined ratio of dry air to a portion of extracted exhaust gas is chosen and logged into the computer 40 as indicated diagrammatically at 40a. Generally, this ratio is between 1:1 to about 10:1 dry air to a portion of extracted exhaust gas; preferably 3:1. For example, assume a 3:1 ratio is chosen in step 40a. Dry air begins flowing through flow meter 48. This flow rate through the flow meter 48 is transmitted to the computer 40 via pressure to current transducer 90 and lead 92. The dry air enters extraction member 18 where it mixes with an extracted portion of exhaust gas drawn from exhaust conduit 14. This dry air and portion of extracted exhaust gas, knows as the diluted gas, flows through flow meter 54. The flow rate through flow member 54 is transmitted to the computer 40 via pressure to current transducer 94 and lead 96. The computer 40 determines and compares the flow rates, subtracting the dilution air flow rate from the diluted gas flow rate. If the comparison of the flow rates through flow meters 48 and 54 in this example is 3 parts of dry air and 4 parts of diluted gas (i.e. one part sample), then the 3:1 predetermined desire ratio is achieved and the computer 40 need not send out signals adjusting the control valves 50 and 56. However, if the ratio is not 3:1, then the computer 40 transmits signals to current to pressure transducers 98 and 102, via leads 100 and 104, which adjust flow control valves 50 and 56 until the 3:1 ratio is achieved. The signals transmitted to the valves and the adjustment of the valves happens very rapidly, several times a second. Thus the system is capable of accurately and dynamically controlling in real time, the ratio of dry air to diluted gas.

In a similar fashion, computer 40 also determines the exhaust flow rate FE of the engine under test. The temperature and pressure transducers 76, 78 and 80, of the dilution air flow rate measuring mechanism 36, are coupled to the computer 40 via leads 106, 108 and 110, respectively. The temperature transducer 76 converts the dilution air temperature signals into electrical signals for processing and calibrating by the computer 40. The pressure transducers 78 and 80 convert the dilution air pressure signals into electrical signals for processing and calibrating by the computer 40. With these three parameters using known subsonic venturi equations, the computer calculates the flow rate FA of the dilution air.

The temperature and pressure transducers 86 and 88, of the bulkstream flow rate measuring mechanism 38, are coupled to the computer via leads 118 and 120. The temperature transducer 86 converts bulkstream gas temperature signals into electrical signals for processing and calibrating by the computer 40. The pressure transducer 88 converts bulkstream gas pressure signals into electrical signals for processing and calibrating by the computer 40. With these two parameters using known sonic venturi equations, the computer calculates the flow rate FS of the bulkstream exhaust gas through the sonic venturi 84.

The computer 40 now having input signals to calculate the mass flow rate of the dilution air and the bulkstream exhaust gas through the subsonic venturi 74 and the sonic venturi 84, respectively, computes the difference between the bulkstream exhaust gas mass flow FS and the dilution air mass flow FA. Once the raw exhaust gas mass flow rate is determined, it can be utilized in the dilution mechanism 22 for controlling the ratio of extracted gas flow that is to be sampled.

Also, the temperature transducer 114 is positioned on the dilution flow circuit 58. The temperature transducer 114 is coupled to the computer 40 via lead 116. The temperature 114 converts temperature signals into electrical signals for processing and calibrating by the computer 40. The computer 40 monitors the temperature of the diluted gas in the flow circuit 58 for providing the system with a means for measuring the temperature of diluted gas flow.

In the embodiment illustrated in FIGS. 1 and 2 the sample is extracted from the raw exhaust produced by the engine under test. The invention may also be implemented in systems where the sample point is located on the diluted exhaust side. Such an embodiment is shown in FIGS. 3 and 4. FIGS. 3 and 4 are similar to FIGS. 1 and 2, except that the sample is extracted via conduit 200. As illustrated, conduit 200 extracts the sample from within test conduit 30. At this point the sample is a diluted sample by virtue of the dilution air added via filtration system 37 and mechanism 36.

While it will be apparent that the preferred embodiment of the invention disclosed is well calculated to fulfill the objects stated above, it will be appreciated that the invention is susceptible to modification, alteration, variation and change without departing from the proper scope or fair meaning of the invention, as defined by the following claims.

What is claimed is:

1. A method for calibrating an apparatus for measuring exhaust mass flow of an internal combustion engine having an exhaust conduit, the apparatus including a test conduit having an exhaust inlet coupled to the exhaust conduit, a subsonic venturi coupled to the test conduit for enabling passage of a fluid, a transducer means coupled with said subsonic venturi for producing a signal, a sonic venturi coupled to the test conduit for enabling passage of a fluid, transducer means coupled with said sonic venturi for producing a signal, and a computer coupled with both transducer means for interpreting the signals, said method comprising:

capping the exhaust inlet of said test conduit;

causing a quantity of fluid to flow through said subsonic venturi, through said test conduit and through said sonic venturi;

measuring the flow through said sonic venturi to produce a first signal;

measuring the flow through said subsonic venturi to produce a second signal;

comparing said first and second signals to determine an error;

adjusting either of said first and second signals to null said error and thereby calibrate said apparatus.

2. The method according to claim 1 wherein a calibration valve is positioned between said subsonic venturi and said test conduit, controlling said quantity of fluid flow through said test conduit and through said sonic venturi.

3. The method according to claim 1 wherein said transducer means coupled with said sonic venturi includes a pressure and temperature transducer measuring the flow through said sonic venturi.

4. The method according to claim 1 wherein said transducer coupled with said subsonic venturi includes a temperature transducer and a pair of pressure transducers for measuring the flow through said subsonic venturi.

* * * * *

(12) EX PARTE REEXAMINATION CERTIFICATE (5059th)
United States Patent
Lewis

(10) Number: US 4,823,591 C1
(45) Certificate Issued: Feb. 15, 2005

(54) CALIBRATION METHOD FOR EXHAUST MASS FLOW MEASURING SYSTEM

(75) Inventor: Gary W. Lewis, Fountain Valley, CA (US)

(73) Assignee: Horiba Instruments Incorporated

Reexamination Request:
No. 90/006,763, Aug. 26, 2003

Reexamination Certificate for:
Patent No.: 4,823,591
Issued: Apr. 25, 1989
Appl. No.: 07/118,195
Filed: Nov. 5, 1987

(51) Int. Cl.[7] ............................................. G01F 25/00
(52) U.S. Cl. ........................................................ 73/1.26
(58) Field of Search ........................................... 73/1.26

(56) References Cited

U.S. PATENT DOCUMENTS

| | | | | |
|---|---|---|---|---|
| 3,699,814 A | * | 10/1972 | Kaufman | 73/863.11 |
| 3,817,100 A | * | 6/1974 | Anderson et al. | 73/861.63 |
| 4,341,107 A | * | 7/1982 | Blair et al. | 73/1.34 |
| 4,586,367 A | * | 5/1986 | Lewis | 73/23.33 |

OTHER PUBLICATIONS

Code of Federal Regulations, Title 40, Protection of Environment, Jul. 1, 1983, pp. 402–440 and 631–637.*

* cited by examiner

*Primary Examiner*—John E Chapman

(57) ABSTRACT

A testing apparatus for sampling the emission content of the source when a portion of the exhaust gas is optionally diluted using clean dry air added near the sample extraction point. A sonic venturi is used to establish a constant mass flow rate from the exhaust system of the engine under test and a subsonic venturi monitors the flow rate of dilution air. Both venturis provide flow rate signals which are substracted to determine the flow rate of the exhaust.

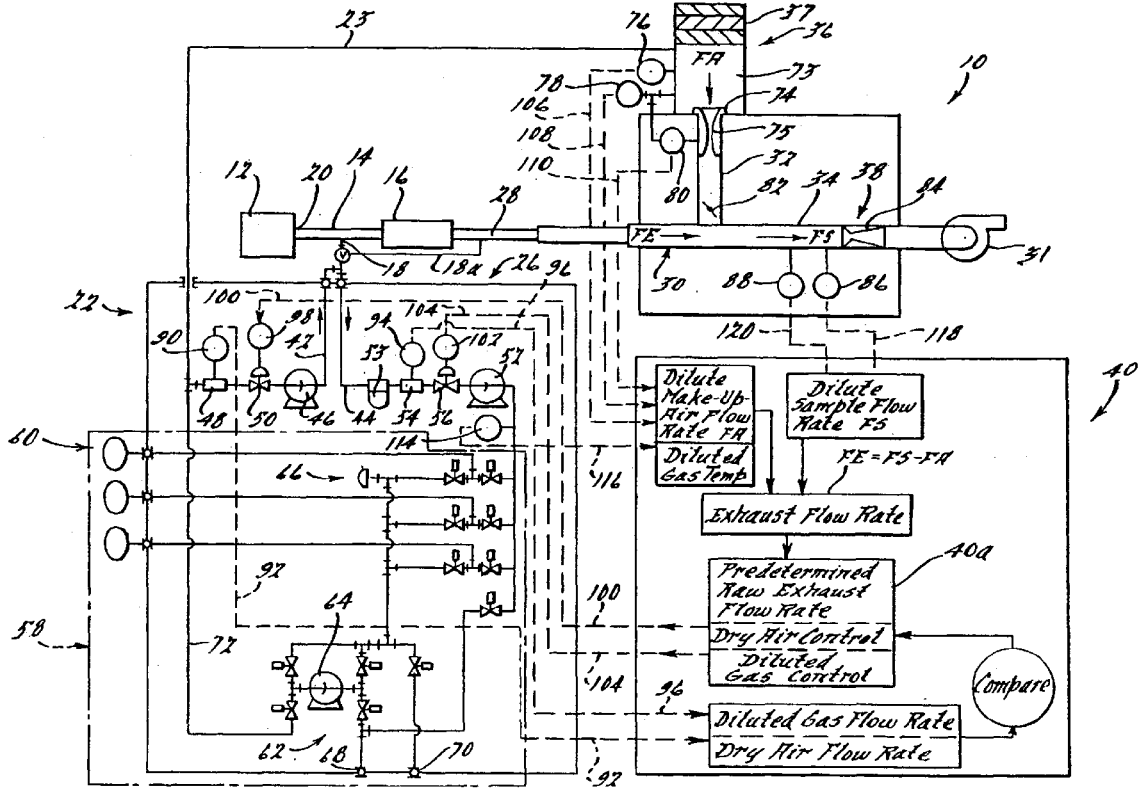

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–4 is confirmed.

* * * * *